United States Patent
Chen

(10) Patent No.: US 6,291,463 B1
(45) Date of Patent: Sep. 18, 2001

(54) 1-(BENZOTHIAZOL-2-YL)-4-(1-PHENYLMETHYL) PIPERAZINES: DOPAMINE RECEPTOR SUBTYPE SPECIFIC LIGANDS

(75) Inventor: Xi Chen, Killingworth, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/345,034

(22) Filed: Jun. 30, 1999

Related U.S. Application Data

(60) Provisional application No. 60/091,210, filed on Jun. 30, 1998.

(51) Int. Cl.[7] .................. A61K 31/496; C07D 417/04
(52) U.S. Cl. ........................... 514/254.02; 544/368
(58) Field of Search ................. 544/368; 514/254.02

(56) References Cited

U.S. PATENT DOCUMENTS

| 3,944,551 | 3/1976 | Regnier et al. ............... 260/268 |
| 5,550,134 | 8/1996 | Audia et al. ................... 514/284 |
| 5,753,595 | 5/1998 | Crawford et al. ............ 504/243 |

FOREIGN PATENT DOCUMENTS

| 30 23 227 A | 1/1982 | (DE) . |
| 0 097 014 A | 12/1983 | (EP) . |
| 2 000 501 A | 1/1979 | (GB) . |
| WO 94/20494 | 9/1994 | (WO) . |
| WO 97 45419 A | 12/1997 | (WO) . |

OTHER PUBLICATIONS

F. Babudri et al., (1983), *Tetrahedron*, vol. 39, No. 9, pp. 1515–1521.
Chemical Abstracts, (1991) vol. 114, No. 21, Abstract No. 207259j.
Chemical Abstracts, (1970), vol. 73, No. 9, Abstract No. 45393d.
Orjales et al., (1995), J. Heterocycl Chem., vol. 32, pp. 707–718, "Synthesis and Structure–Activity Relationship of New Piperidinyl and Piperazinyl Derivatives as Antiallergics".
Monge et al., (1994), J. Med. Chem., vol. 37, pp. 1320–1325, "Synthesis of 2–Piperazinylbenzothiazole and 2–Piperazinylbenzoxazole Derivatives with 5–HT3 Antagonist and 5–HT4 Agonist Properties".
Verderame, (Jun. 1972), J. Med. Chem., vol. 15, No. 6, "1, 4–Disubstituted Piperazines, 3. Piperazinylbenzothiazole", pp. 693–694.

*Primary Examiner*—Emily Bernhardt
(74) *Attorney, Agent, or Firm*—McDonnellBoehnen Hulbert & Berghoff; Steven J. Sarussi

(57) ABSTRACT

Disclosed are compounds of the formula:

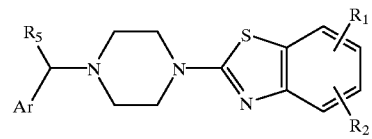

or pharmaceutically acceptable addition salts thereof wherein:

$R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano or trifluoromethyl;

Ar represents aryl or heteroaryl, each of which is optionally substituted with $R_3$, $R_4$ and/or $R_4$;

$R_3$, $R_4$, and $R_6$ independently represent hydrogen, halogen, hydroxy, $C_1$–$C_6$ alkyl, $C_1$–$C_6$ alkoxy, perfluoro($C_1$–$C_6$)alkyl, perfluoro($C_1$–$C_6$)alkoxy, or $SO_2NH_2$; or $R_3$ and $R_4$ together with the atoms to which they are attached represent a ring having 5–7 atoms; and $R_5$ represents hydrogen or $C_1$–$C_6$ alkyl, which compounds are useful for the treatment and/or prevention of neuropsychological disorders including, but not limited to, schizophrenia, mania, dementia, depression, anxiety, compulsive behavior, substance abuse, Parkinson-like motor disorders and motion disorders related to the use of neuroleptic agents.

8 Claims, No Drawings

1-(BENZOTHIAZOL-2-YL)-4-(1-PHENYLMETHYL) PIPERAZINES: DOPAMINE RECEPTOR SUBTYPE SPECIFIC LIGANDS

This application claims benefit of priority from U.S. Provisional Appl. Ser. No. 60/091,210 filed Jun. 30, 1998.

BACKGROUND OF THE INVENTION

1. Field of the Invention

This invention relates to 1-(benzothiazol-2-yl)-4-(1-phenylmethyl)piperazines and pharmaceutical compositions containing such compounds. It also relates to the use of such compounds in the treatment or prevention of psychotic disorders such as schizophrenia and other central nervous system diseases.

2. Description of the Related Art

The therapeutic effect of conventional antipsychotics, known as neuroleptics, is generally believed to be exerted through blockade of dopamine receptors. However, neuroleptics are frequently responsible for undesirable extrapyramidal side effects (EPS) and tardive dyskinesias, which are attributed to blockade of $D_2$ receptors in the striatal region of the brain. The dopamine $D_4$ receptor subtype has recently been identified (Nature, 350: 610 (Van Tol et al., 1991); Nature, 347: 146 (Sokoloff et al., 1990)). Its unique localization in limbic brain areas and its differential recognition of various antipsychotics indicates that the $D_4$ receptor plays a major role in the etiology of schizophrenia. Selective $D_4$ antagonists are considered effective antipsychotics free from the neurological side effects displayed by conventional neuroleptics.

J. Heterocycl. Chem., 32: 707–718 (Orjales et al., 1995) discloses piperazinebenzothiazole derivatives said to be useful as antihistaminics.

J. Med. Chem., 37: 1320–1325 (Monge et al., 1994) discloses piperazinebenzothiazole derivatives as $5-HT_3$ antagonists and $5-HT_4$ agonists.

Published International Application WO 9420494 discloses piperazinebenzothiazole derivatives said to be capable of stimulating gastrointestinal motility.

SUMMARY OF THE INVENTION

This invention provides novel compounds of Formula I which interact with dopamine receptor subtypes. Accordingly, a broad aspect of the invention is directed to a compound of Formula I:

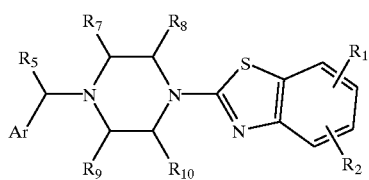

I or pharmaceutically acceptable addition salts thereof wherein:

$R_1$ and $R_2$ are the same or different and represent hydrogen, halogen, $C_1-C_6$ alkyl, $C_1-C_6$ alkoxy, $C_1-C_6$ alkylthio, hydroxy, amino, mono- or di($C_1-C_6$) alkylamino, cyano or trifluoromethyl;

Ar represents aryl or heteroaryl, each of which is optionally substituted with $R_3$, $R_4$ and/or $R_6$;

$R_7$, $R_8$, $R_9$, and $R_{10}$ are the same or different and represent hydrogen or $C_1-C_6$ alkyl;

$R_3$, $R_4$, and $R_6$ independently represent hydrogen, halogen, hydroxy, $C_1-C_6$ alkyl, $C_1-C_6$ alkoxy, perfluoro($C_1-C_6$)alkyl, perfluoro($C_1-C_6$)alkoxy, or $SO_2NH_2$, provided that when Ar is phenyl and two or three of $R_3$, $R_4$, and $R_6$ are methoxy, no two methoxy groups may be positioned ortho to each other on the phenyl ring; or $R_3$ and $R_4$ together with the atoms to which they are attached represent a ring having 5–7 atoms;

$R_5$ represents hydrogen or $C_1-C_6$ alkyl.

Dopamine $D_4$ receptors are concentrated in the limbic system (Science, 265: 1034 (Taubes, 1994)) which controls cognition and emotion. Therefore, compounds that interact with these receptors are useful in the treatment of cognitive disorders. Such disorders include cognitive deficits which are a significant component of the negative symptoms (social withdrawal and unresponsiveness) of schizophrenia. Other disorders include those involving memory impairment or attention deficit disorders.

Compounds of the present invention demonstrate high affinity and selectivity in binding to the $D_4$ receptor subtype. These compounds are therefore useful in treatment of a variety of neuropsychological disorders, such as, for example, schizophrenia, psychotic depression and mania. Other dopamine-mediated diseases such as Parkinsonism and tardive dyskinesias can also be treated directly or indirectly by modulation of $D_4$ receptors.

Compounds of this invention are also useful in the treatment of depression, memory-impairment or Alzheimer's disease by modulation of $D_4$ receptors since they exist selectively in areas known to control emotion and cognitive functions.

Thus, in another aspect, the invention provides methods for treatment and/or prevention of neuropsychochological or affective disorders including, for example, schizophrenia, mania, dementia, depression, anxiety, compulsive behavior, substance abuse, memory impairment, cognitive deficits, Parkinson-like motor disorders, e.g., Parkinsonism and dystonia, and motion disorders related to the use of neuroleptic agents. In addition, the compounds of the invention are useful in treatment of depression, memory-impairment or Alzheimer's disease. Further, the compounds of the present invention are useful for the treatment of other disorders that respond to dopaminergic blockade, e.g., substance abuse and obsessive compulsive disorder. These compounds are also useful in treating the extrapyramidal side effects associated with the use of conventional neuroleptic agents.

In yet another aspect, the invention provides pharmaceutical compositions comprising compounds of Formula I.

In another aspect, the invention provides intermediates useful in the preparation of compounds of Formula I.

DETAILED DESCRIPTION OF THE INVENTION

As noted above, this invention provides compounds of Formula I which interact with dopamine subtypes.

Preferred compounds of Formula I are those where $R_1$ and $R_2$ are hydrogen. More preferred compounds of Formula I are those wherein $R_1$ and $R_2$ are hydrogen and Ar is not unsubstituted phenyl, i.e., phenyl substituted with at least one non-hydrogen substituent. Particularly preferred compounds of Formula I are those where Ar is phenyl or naphthyl, each of which is optionally substituted with up to three of the groups listed above. In these particularly preferred compounds, when Ar is phenyl and $R_1$ and $R_2$ are hydrogen, $R_3$, $R_4$, and $R_6$ may not all be hydrogen simultaneously. Other preferred compounds of Formula I are those where $R_7$, $R_8$, $R_9$, and $R_{10}$ are hydrogen or $C_1$–$C_2$ alkyl.

In preferred compounds, when Ar is phenyl and two or three of $R_3$, $R_4$, and $R_6$ are methoxy or ethoxy, no two methoxy groups may be methoxy groups positioned ortho to each other; more preferably no methoxy group may be positioned ortho to another methoxy group or to an ethoxy group. Even more preferably, when Ar is phenyl and two or three of $R_3$, $R_4$, and $R_6$ are methoxy or ethoxy, no methoxy or ethoxy group may be in an ortho position on the phenyl ring with respect to another methoxy or ethoxy group. Highly preferred compounds of the invention include those where one and only one of $R_3$, $R_4$, and $R_6$ is $C_1$–$C_6$ alkoxy when Ar is phenyl.

More preferred compounds of Formula I are those where Ar is

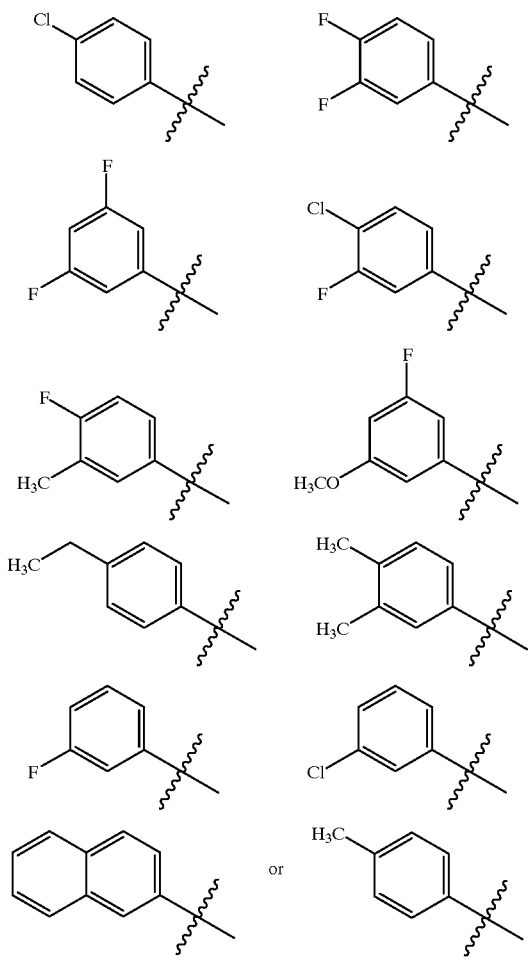

Preferred compounds of the invention include those of Formula II:

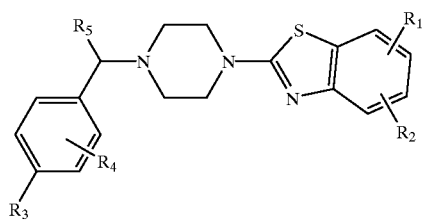

wherein $R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano or trifluoromethyl;

$R_3$ and $R_4$ are the same or different and represent hydrogen, halogen, hydroxy, $C_1$–$C_6$ alkyl, trifluoromethyl, trifluoromethoxy, or $SO_2NH_2$, provided that not both $R_3$ and $R_4$ are hydrogen simultaneously; and $R_5$ represents hydrogen or $C_1$–$C_6$ alkyl.

Preferred compounds of Formula II include those where $R_5$ is hydrogen. Other preferred compounds of Formula II include those where $R_5$ is hydrogen, and $R_3$ is halogen or $C_1$–$C_6$ alkyl. More preferred compounds of Formula II are where $R_4$ is halogen, $R_5$ is hydrogen, and $R_3$ is halogen or $C_1$–$C_6$ alkyl. Particularly preferred compounds of Formula II are those where $R_1$ and $R_2$ are hydrogen, $R_4$ is halogen, $R_5$ is hydrogen, and $R_3$ is halogen or $C_1$–$C_6$ alkyl. A highly preferred group of compounds are those where $R_4$ is halogen in the meta position of the phenyl ring, $R_5$ is hydrogen, and $R_3$ is halogen or $C_1$–$C_6$ alkyl.

Highly preferred compounds of Formula II are those where the phenyl carrying $R_3$ and $R_4$ is selected from:

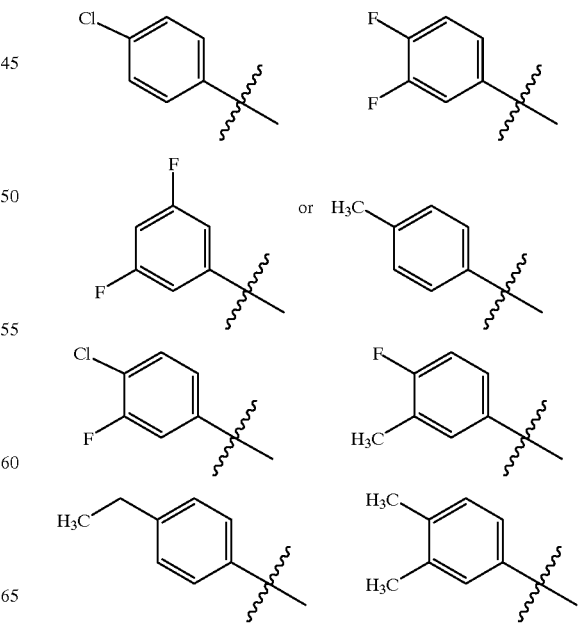

-continued

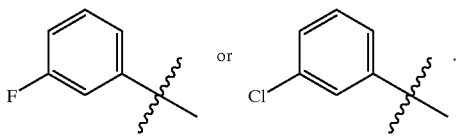

Other preferred compounds of the invention are those of Formula III:

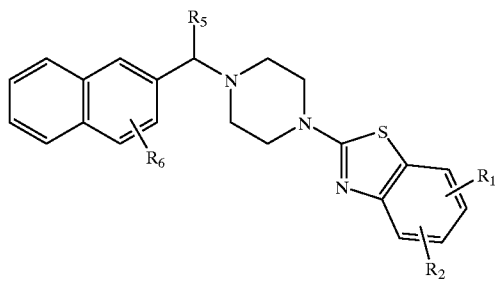

III wherein:
R$_1$ and R$_2$ are the same or different and represent hydrogen, halogen, C$_1$–C$_6$ alkyl, C$_1$–C$_6$ alkoxy, C$_1$–C$_6$ alkylthio, hydroxy, amino, mono- or di(C$_1$–C$_6$) alkylamino, cyano or trifluoromethyl;

R$_6$ represents hydrogen, halogen, hydroxy, C$_1$–C$_6$ alkyl, trifluoromethyl, trifluoromethoxy, or SO$_2$NH$_2$; and R$_5$ represents hydrogen or C$_1$–C$_6$ alkyl.

Preferred compounds of Formula III include those where R$_5$ is hydrogen. Other preferred compounds of Formula III include those where R$_5$ is hydrogen, and R$_6$ is hydrogen, halogen or C$_1$–C$_6$ alkyl. More preferred compounds of Formula III are where R$_6$ is hydrogen. Particularly preferred compounds of Formula III are those where R$_1$, R$_2$, and R$_5$ are hydrogen.

The invention also provides intermediates useful in preparing compounds of Formula I. These intermediates have Formulae IV and V.

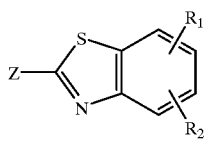

IV where R$_1$ and R$_2$ are defined as above for Formula I; and Z is a leaving group, such as halogen.

Preferred compounds of Formula IV are where R$_1$ and R$_2$ are hydrogen, methyl or ethyl; and Z is chloro.

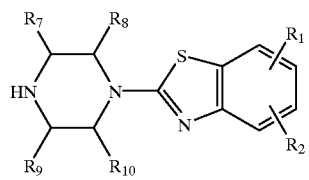

V where R$_1$, R$_2$, and R$_7$–R$_{10}$ are defined as above for Formula I.

Preferred compounds of Formula V are where R$_1$ and R$_2$ are hydrogen. Particularly preferred compounds of Formula V are those where R$_1$, R$_2$, and R$_7$–R$_{10}$ are hydrogen, methyl, or ethyl.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds in Table I and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)$_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

Where a compound exists in various tautomeric forms, the invention is not limited to any one of the specific tautomers. The invention includes all tautomeric forms of a compound.

By "C$_1$–C$_6$ alkyl" or "lower alkyl" in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred C$_1$–C$_6$ alkyl groups are methyl, ethyl, propyl, butyl, cyclopropyl and cyclopropylmethyl.

By "C$_1$–C$_6$ alkoxy" or "lower alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By aryl or "Ar" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred Ar groups are phenyl and 2-naphthyl.

By aryl or "Ar" is also meant heteroaryl groups where heteroaryl is defined as 5, 6, or 7 membered aromatic ring systems having at least one hetero atom selected from the group consisting of nitrogen, oxygen and sulfur. Examples of heteroaryl groups are pyridyl, pyrimidinyl, pyrrolyl, pyrazolyl, pyrazinyl, pyridazinyl, oxazolyl, furanyl, quinolinyl, isoquinolinyl, thiazolyl, and thienyl, which can optionally be substituted with, e.g., halogen, lower alkyl, lower alkoxy, lower alkylthio, trifluoromethyl, lower acyloxy, aryl, heteroaryl, and hydroxy.

As noted above, $R_3$ and $R_4$ may be connected together to form another ring with the atoms to which they are attached on the parent aryl or heteroaryl group. Thus, $R_3$ and $R_4$ may represent an alkylene, alkenylene, alkyleneoxy, alkylenedioxy, alkyleneazo, or alkylenediazo chain that together with the atoms to which they are attached form a ring having 5–7 atoms. For example, Ar may be an optionally substituted naphthyl group or a bicyclic oxygen-containing group of the formula

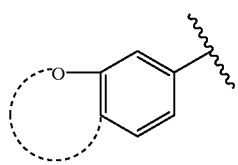

wherein the heterocyclic oxygen containing ring has a total of from 5 to 7 ring members, the heterocyclic ring being saturated or unsaturated, and optionally substituted.

Preferred examples of bicyclic oxygen-containing groups are:

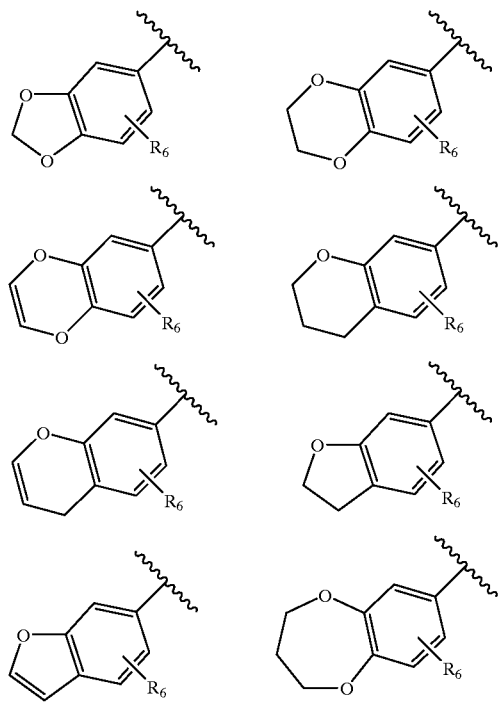

As an additional example, Ar may be a bicyclic nitrogen-containing group of the formula

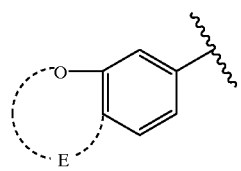

wherein E is methylene or nitrogen and the heterocyclic oxygen containing ring has a total of from 5 to 7 ring members, the heterocyclic ring being saturated or unsaturated, and optionally substituted.

Preferred examples of bicyclic nitrogen-containing groups are:

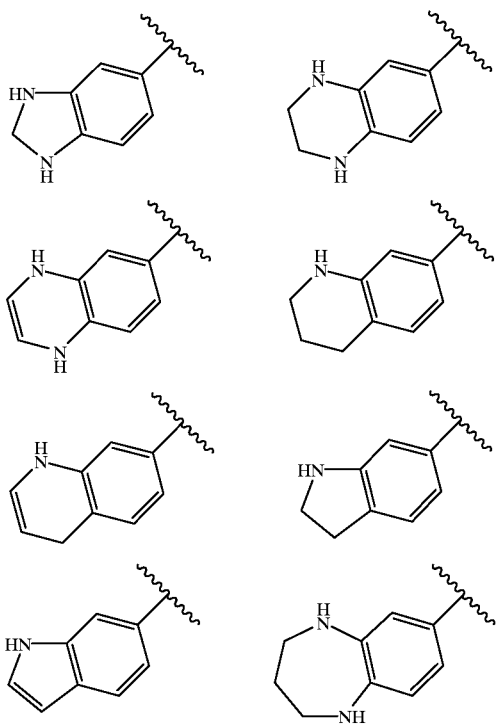

Representative 1-(benzothiazol-2-yl)-4-(1-phenylmethyl) piperazines of the present invention are shown in Table 1. The number below each compound is its compound number.

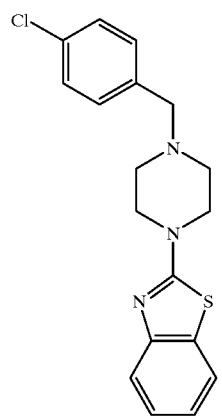

1

-continued

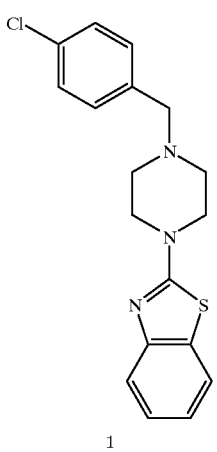

1

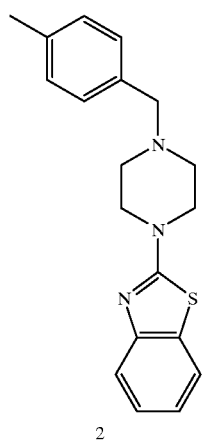

2

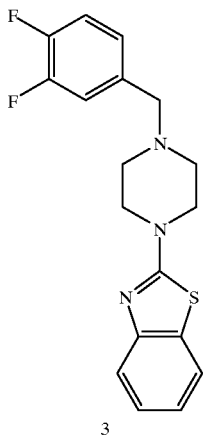

3

-continued

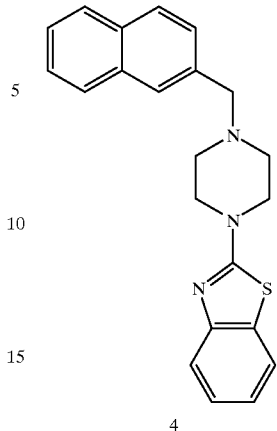

4

The invention also pertains to the use of compounds of general Formula I in the treatment of neuropsychological disorders. The selective interaction of compounds of the invention with dopamine receptors results in the pharmacological activity of these compounds.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate;

granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative synthesis of the 1-(benzothiazol-2-yl)-4-(1-phenylmethyl)-piperazines of the invention is presented in Scheme I.

Scheme I

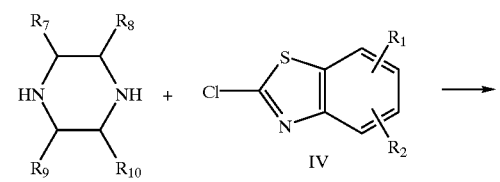

-continued

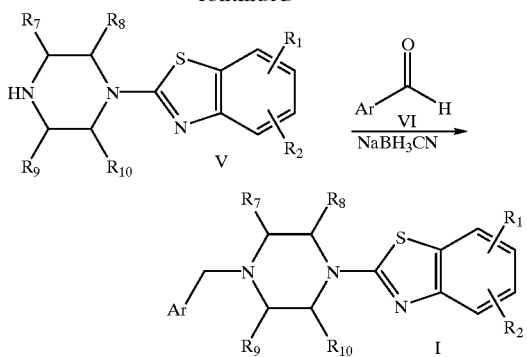

wherein Ar, $R_1$, $R_2$, $R_7$, $R_8$, $R_9$, and $R_{10}$ are as defined above for Formula 1.

As shown in Scheme I, a 2-chlorobenzothiazole IV may be condensed with an appropriately substituted piperazine to provide a 1-(benzothiaol-2-yl)piperazine V. Piperazine V may then be reductively alkylated with an arylaldehyde VI using, for example, sodium cyanoborohydride to provide a 1-(benzothiaol-2-yl)-4-(1-phenylmethyl)piperazine of Formula I.

Alternatively, compounds of Formula I may be prepared according to the Scheme II.

Scheme II

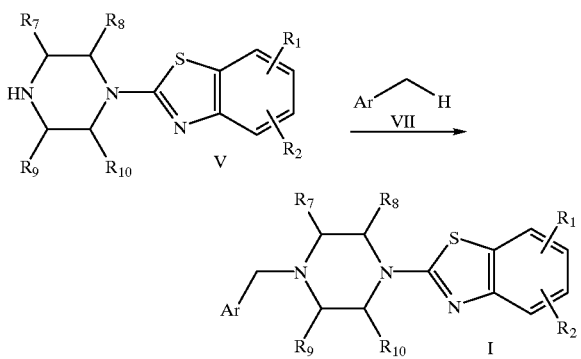

wherein Ar, $R_1$, $R_2$, $R_7$, $R_8$, $R_9$, and $R_{10}$ are as defined above for Formula 1, and X represents a leaving group, e.g., a halide.

As illustrated in Scheme II, a 1-(benzothiaol-2-yl) piperazine V may be alkylated using an appropriate arylmethyl compound VII where X is a halide, sulphonate ester or the like to provide a 1-(benzothiaol-2-yl)-4-(1-phenylmethyl)piperazine of Formula 1.

In either of these approaches to the compounds of Formula I, those having skill in the art will recognize that the starting materials may be varied and additional steps employed to produce compounds encompassed by the present invention.

The disclosures of all articles and references mentioned in this application, including patents, are incorporated herein by reference.

The preparation of the compounds of the present invention is illustrated further by the following examples which are not to be construed as limiting the invention in scope or spirit to the specific procedures and compounds described in them.

The starting materials and various intermediates may be obtained from commercial sources, prepared from commercially available organic compounds, or prepared using well known synthetic methods.

EXAMPLE 1

1. 1-(Benzothiazol-2-yl)piperazine

A solution of 2-chlorobenzothiazole (5 g) in 20 mL of toluene is added dropwise to a refluxing solution of piperazine (20 g) in 150 mL of toluene. The solution is heated for an additional 24 hours, and after cooling at 0° C. for about 30 minutes, filtered. The filtrate is extracted with 10% acetic acid and the aqueous extracts are washed with ether, basified and extracted with dichloromethane. The dichloromethane layer is washed with water, dried and concentrated. The concentrated material is placed under vacuum overnight (6.8 g, m.p. 63–64° C.). $^1$H NMR (CDCl$_3$) 7.62 (d, J=8.0 Hz, 1H), 7.55 (d, J=8.0 Hz, 1H), 7.29 (td, J=7.6, 1.2 Hz, 1H), 7.07 (t, J=8.0 Hz, 1H), 3.61 (t, J=5.2 Hz, 4H), 3.00 (t, J=5.2 Hz, 4H).

2. 1-(Benzothiazol-2-yl)-4-(1-[3-chlorophenyl]methyl) piperazine hydrochloride

A solution of 1-(benzothiazol-2-yl)piperazine (220 mg, 1.0 mmol) and 3-chlorobenzaldehyde (150 mg) in methanol (10 mL) is made and the pH adjusted to about 4 using acetic acid. Sodium cyanoborohydride (500 mg) is then added and the reaction mixture stirred at room temperature overnight during which time a white precipitate forms. The precipitate, 1-(Benzothiazol-2-yl)-4-(1-[3-chlorophenyl]-methyl) piperazine (Compound 5), is collected by vacuum filtration and washed with methanol. The hydrochloride salt, Compound 5A, is obtained from an isopropanol solution (320 mg, 88%, m.p. 238–241° C.). $^1$H NMR (DMSO) 7.82 (d, J=7.3 Hz, 1H), 7.76 (s, 1H), 7.58 (d, J=7.3 Hz, 1H), 7.51 (m, 4H), 7.31 (td, J=7.3, 1.2 Hz, 1H), 7.12 (t, J=7.3 Hz, 1H), 4.38 (s br, 2H), 4.15 (d br, J=12.8 Hz, 2H), 3.66 (t br, J=12.2 Hz, 2H). 3.39 (d br, J=11.6 Hz, 2H), 3.20 (s br, 2H).

EXAMPLE 2

1-(Benzothiazol-2-yl)-4-(1-[4-chlorophenyl]methyl) piperazine hydrochloride

A solution of 1-(benzothiazol-2-yl)piperazine (220 mg, 1.0 mmol) and 4-chlorobenzyl chloride (180 mg) in acetonitrile (10 mL) containing potassium carbonate (500 mg) is stirred and heated at 60° C. for 4 h. After cooling, the reaction is partitioned between ether and water and the organic layer is extracted with 1 N HCl. The combined acid extracts are basified and extracted with chloroform. The organic layer is dried and concentrated to provide the product as a white solid (Compound 1, 300 mg, 87%). The oxalate salt, Compound 1A, is obtained from an isopropanol solution (m.p. 216–218° C.). $^1$H NMR (DMSO) 7.75 (d, J=7.3 Hz, 1H), 7.40 (m, 5H), 7.29 (t, J=7.6 Hz, 1H), 7.06 (t, J=7.2 Hz, 1H), 3.65 (s br, 2H), 3.36 (s br, 4H), 2.60 (s br, 4H).

EXAMPLE 3

The following compounds are prepared essentially according to the methods set forth above in Examples 1 and 2:

(a) 1-(benzothiazol-2-yl)-4-(1-[4-methylphenyl]methyl) piperazine oxalate (Compound 2A, m.p. 243–244° C.)

(b) 1-(benzothiazol-2-yl)-4-(1-[3,4-difluorophenyl] methyl)piperazine oxalate (Compound 3A, m.p. 223–224° C.)

(c) 1-(benzothiazol-2-yl)-4-(1-[2-naphthyl]methyl) piperazine oxalate (Compound 4A, m.p. 158–160° C.)

EXAMPLE 4

Assay for $D_2$ and $D_4$ Receptor Binding Activity

The utility of compounds of this invention is indicated by the assays for dopamine receptor subtype affinity described below.

Pellets of COS cells containing recombinantly produced $D_2$ or $D_4$ receptors from African Green monkey were used for the assays. The sample is homogenized in 100 volumes (w/vol) of 0.05 M Tris HCl buffer at 4° C. and pH 7.4. The sample is then centrifuged at 30,000×g and resuspended and rehomogenized. The sample is then centrifuged as described and the final tissue sample is frozen until use. The tissue is resuspended 1:20 (wt/vol) in 0.05 M Tris HCl buffer containing 100 mM NaCl.

Incubations are carried out at 48° C. and contain 0.4 ml of tissue sample, 0.5 nM $^3$H-YM 09151-2 (Nemonapride, cis-5-Chloro-2-methoxy-4-(methylamino)-N-(2-methyl-2-(phenylmethyl)-3-pyrroli-dinyl)benzamide) and the compound of interest in a total incubation of 1.0 ml. Nonspecific binding is defined as that binding found in the presence of 1 mM spiperone; without further additions, nonspecific binding is less than 20% of total binding. Binding characteristics for representative compounds of the invention for the $D_2$ and $D_4$ receptor subtypes are shown in Table 2.

TABLE 2

| Compound Number[1] | $D_4$ $K_i$ (nM) | $D_2$ $K_i$ (nM) |
| --- | --- | --- |
| 1A | 14 | >4000 |
| 2A | 25 | 3508 |
| 4A | 76 | 3508 |

The above data are representative of the $K_i$ values for compounds of the invention; all compounds of the invention are active in the above assay. Further, compounds of the invention generally possess a Ki value for the dopamine $D_4$ receptor subtype of below about 100 nM.

The binding constants of compounds of Formula I for the $D_4$ receptor, expressed in nM, generally range from about 5 nanomolar (nM) to about 100 nanomolar (nM). These compounds typically have binding constants for the $D_2$ receptor of from about 500 nM to at least 4000 nM. Thus, the compounds of the invention are generally at least about 5 time more selective for the $D_4$ receptor than the $D_2$ receptor. Preferably, these compounds are at least 10, and more preferably at least 20–50, times more selective for the $D_4$ receptor than the $D_2$ receptor. Most preferably, these compounds are at least 100 times more selective for the $D_4$ receptor than the $D_2$ receptor.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

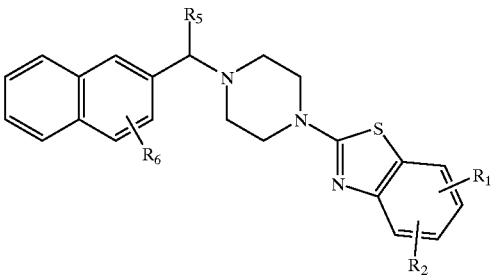

or pharmaceutically acceptable addition salts thereof wherein:

$R_1$ and $R_2$ are the same or different and represent hydrogen, halogen, $C_1$–$C_6$ alkyl, $C_1$–$C_6$ alkoxy, $C_1$–$C_6$ alkylthio, hydroxy, amino, mono- or di($C_1$–$C_6$) alkylamino, cyano or trifluoromethyl;

$R_6$ represents hydrogen, halogen, hydroxy, $C_1$–$C_6$ alkyl, trifluoromethyl, trifluoromethoxy, or $SO_2NH_2$; and $R_5$ represents hydrogen or $C_1$–$C_6$ alkyl.

2. A compound according to claim 1, wherein $R_5$ is hydrogen.

3. A compound according to claim 2, wherein $R_6$ is halogen or $C_1$–$C_6$ alkyl.

4. A compound according to claim 2, wherein $R_6$ is halogen.

5. A compound according to 4, wherein $R_1$ and $R_2$ are hydrogen.

6. A compound which is selected from:
   1-(benzothiazol-2-yl)-4-(1-[4-chlorophenyl]methyl) piperazine oxalate;
   1-(benzothiazol-2-yl)-4-(1-[4-methylphenyl]methyl) piperazine oxalate;
   1-(benzothiazol-2-yl)-4-(1-[3,4-difluorophenyl]methyl) piperazine oxalate;
   1-(benzothiazol-2-yl)-4-(1-[2-naphthyl]methyl) piperazine oxalate;
   1-(benzothiazol-2-yl)-4-(1-[3-chlorophenyl]methyl) piperazine hydrochloride; and
   1-(benzothiazol-2-yl)-4-(1-[4-chlorophenyl]methyl) piperazine oxalate.

7. A compound which is selected from 1-(benzothiazol-2-yl)-4-(1-[3,4-difluorophenyl]methyl)piperazine and 1-(benzothiazol-2-yl)-4-(1-[2-naphthyl]methyl)piperazine.

8. A pharmaceutical composition comprising a therapeutically effective amount of a compound or salt according to claim 1 and a pharmaceutically acceptable carrier.

* * * * *